United States Patent [19]
Wideman et al.

[11] Patent Number: 5,902,889
[45] Date of Patent: May 11, 1999

[54] PROCESS FOR HYDROGENATION OF CARBON-CARBON DOUBLE BONDS OF A WATER-SOLUBLE OLEFINICALLY UNSATURATED CARBOXYLIC ACID SALT

[75] Inventors: Lawson Gibson Wideman, Tallmadge; Denise Jeannette Keith, Akron, both of Ohio

[73] Assignee: The Goodyear Tire & Rubber Company, Akron, Ohio

[21] Appl. No.: 08/933,204

[22] Filed: Sep. 18, 1997

[51] Int. Cl.$^6$ ..................................................... C07C 51/36
[52] U.S. Cl. ........................... 554/147; 554/141; 562/598; 530/223; 530/224; 524/599
[58] Field of Search ..................................... 554/141, 147; 530/223, 224; 524/599; 562/598

[56] References Cited

U.S. PATENT DOCUMENTS

| | | | |
|---|---|---|---|
| 4,452,950 | 6/1984 | Wideman | 525/339 |
| 4,895,911 | 1/1990 | Mowdood et al. | 525/346 |
| 5,221,714 | 6/1993 | Parker | 525/237 |
| 5,424,356 | 6/1995 | Parker et al. | 524/555 |

*Primary Examiner*—Gary Geist
*Assistant Examiner*—Deborah D. Carr
*Attorney, Agent, or Firm*—Bruce J Hendricks

[57] ABSTRACT

A process for hydrogenating carbon-carbon double bonds of a water-soluble olefinically unsaturated carboxylic acid salt which comprises (a) combining an aqueous solution of an olefinically unsaturated carboxylic acid salt with
   (1) an oxidant selected from the group consisting of oxygen, air and hydroperoxides;
   (2) a reducing agent selected from hydrazine and hydrates thereof; and
   (3) a metal ion activator;
(b) heating the mixture to a temperature from 0° C. to the reflux temperature of the reaction mixture; and
(c) neutralizing the pH of the reaction mixture.

12 Claims, No Drawings

PROCESS FOR HYDROGENATION OF CARBON-CARBON DOUBLE BONDS OF A WATER-SOLUBLE OLEFINICALLY UNSATURATED CARBOXYLIC ACID SALT

BACKGROUND OF THE INVENTION

Olefinically unsaturated carboxylic acids include rosin acids and fatty acids. These acids are a common additive to rubber compounds. When converted to a more saturated form, the more saturated fatty acids are easier to handle and the more saturated rosin acids render the rubber to which they are added more tacky. One way to reduce the level of unsaturation in an unsaturated carboxylic acid is to heat the unsaturated acid to a high temperature and high pressure in the presence of hydrogen. Obviously, the use of such high reaction conditions significantly contribute to increasing the cost of producing such acids with reduced unsaturation.

SUMMARY OF THE INVENTION

The present invention relates to a process for hydrogenating carbon-carbon double bonds of a water-soluble olefinically unsaturated carboxylic acid salt.

DETAILED DESCRIPTION OF THE INVENTION

There is disclosed a process for hydrogenating carbon-carbon double bonds of a water-soluble olefinically unsaturated carboxylic acid salt which comprises
- (a) combining an aqueous solution of an olefinically unsaturated carboxylic acid salt with
  - (1) an oxidant selected from the group consisting of oxygen, air and hydroperoxides;
  - (2) a reducing agent selected from hydrazine and hydrates thereof; and
  - (3) a metal ion activator;
- (b) heating the mixture to a temperature from 0° C. to the reflux temperature of the reaction mixture; and
- (c) neutralizing the pH of the reaction mixture.

The present invention relates to hydrogenating carbon-carbon double bonds of a water-soluble olefinically unsaturated carboxylic acid salt. The water-soluble olefinically unsaturated carboxylic acid salts are derived from olefinically unsaturated carboxylic acids. The carboxylic acids include fatty acids, rosin acids and mixtures thereof. Representative examples of fatty acids include oleic acid, 9,12-linoleic acid, 9,11-linoleic acid and 9,12,15-linolenic acid. Representative examples of rosin acids include abietic acid, levopimaric acid, neoabietic acid, palustric acid, dehydroabietic acid, pimaric acid, isopimaric acid, Δ-isopimaric acid, elliotinoic acid, sandaracopimaric acid and mixtures thereof. Preferably, the acids are oleic acid, 9,12-linoleic acid, 9,11-linoleic acid, 9,12,15-linolenic acid, abietic acid and levopimaric acid.

One particular class of olefinically unsaturated carboxylic acids are contained in tall oil fatty acids. Tall oil fatty acids (TOFA) are obtained by the distillation of crude tall oil. Crude tall oil, a by-product of the Kraft pulping process, is a mixture of fatty acids, rosin acids and unsaponifiables. These components are separated from one another by a series of distillations. The fatty acids are predominantly 18-carbon straight-chain mono- or diunsaturated fatty acids. Specifically, the fatty acids may include oleic acid, 9,12-linoleic acid, 9,11-linoleic acid (conjugated linoleic acid), 9,12,15-linolenic acid, stearic acid, pinolenic acid, eicosenoic acid, palmitic acid, palmitoleic acid, magaric acid, octadecadienoic acid, octadecatrienoic acid and the like. Generally speaking, the mixture of tall oil acids for use in the present invention contain from about 28 percent to about 55 percent of oleic acid, from about 25 percent to about 40 percent by weight of linoleic acid and from about 4 percent to about 20 percent of the conjugated linoleic acid. The remaining fatty acid components may comprise from about 1 to 15 percent by weight of any of the remaining above-mentioned fatty acids; for example, from about 1 percent to about 4 percent of stearic acid. In addition to the fatty acids, the tall oil fatty acid mixture may contain minor amounts of rosin acids. Rosin acids that are generally found in tall oil fatty acid mixtures may include abietic acid, dehydroabietic acid, palustric/levopimaric acid, 9,10-secodehydroabietic acid, pimaric acids, tetrahydroabietic acid, isopimaric acid, neoabietic acid and the like. The respective weight percentages of the fatty acids may be determined according to ASTM D-803-65. The respective weight percentages of the rosin acids may be determined by ASTM D-1240-54.

Tall oil fatty acid mixtures are commercially available from a number of refiners such as Arizona Chemical Company of Panama City, Fla.; and Georgia Pacific, Hercules, Monsanto-Emery, Reichhold, Sylvachem, Union Camp and Westvaco of North Charleston, S.C.

In order to render the above carboxylic acids water-soluble, it is preferred to convert such acids to their salt form. While any variety salt forms can be prepared and used, generally speaking, the sodium, potassium and lithium salts are recommended based on their availability and cost. Representative sources of such cations are sodium hydroxide, sodium bicarbonate, potassium hydroxide, potassium bicarbonate and lithium hydroxide.

The above cation containing source is reacted with the carboxylic acid to form the respective carboxylic acid salt. The mole ratio of the cation source and the unsaturated carboxylic acid may vary. Generally speaking, the mole ratio of the cation source to carboxylic acid ranges from about 0.8:1 to 1:0.8. Preferably, the mole ratio of the cation source to carboxylic acid ranges from about 1:0.9 to 1:1.

Once formed, the olefinically unsaturated carboxylic acid salt is solubilized in an aqueous solution. The concentration in the aqueous solution many be from 1 percent by weight of the overall aqueous solution to complete saturation. Preferably, the concentration ranges from 5 to 20 percent by weight. The concentration of the carboxylic acid salt in the aqueous solution is not deemed as limiting feature but rather a question of practicality.

The hydrogenation reaction is carried out in an open or closed vessel. The reaction temperature is 0° to 300° C., preferably 20° to 150° C. Temperatures of not more than 100° C. are preferred so as to ensure selective hydrogenation and inhibit undesirable sidereactions. Pressure vessels are not required; however, pressures can range from atmospheric pressure to 300 kg/cm$^2$.

A reducing agent selected from hydrazine and hydrates thereof is added to the aqueous solution. The mole ratio of the hydrazine or hydrate thereof to moles of olefinic double bonds ranges from about 10:1, with a range of from 6:1 to 4:1 being preferred.

Metal ions or salts that are reduced by hydrazine are used as metal ion initiators in the hydrogenation reaction of the present invention. When hydroperoxides are used as the oxidant, a lesser amount of metal ion initiator is needed. However, an excess of metal ion initiator is generally used. The following list is representative of the metals whose ions or salts will react with hydrazine and are, therefore, useful in the present invention: antimony, arsenic, bismuth, cerium, chromium, cobalt, copper, gold, iron, lead, manganese, mercury, molybdenum, nickel, osmium, palladium, platinum, silver and tin. The preferred metals are cobalt, copper, iron, lead, nickel, silver and tin.

Oxidants useful in the instant invention are oxygen, air and hydrogen peroxide. Other oxidants may be chosen form commercially available hydroperoxides. Representative hydroperoxides are cumyl hydroperoxide, t-butyl hydroperoxide, p-menthane hydroperoxide and the like. The preferred oxidant is air.

The following examples are presented to illustrate the present invention. All parts are parts by weight unless indicated otherwise.

EXAMPLE 1

A 4-liter stainless beaker was mounted on a stirrer-hot plate and equipped with a Teflon-coated stirrer bar, a thermocouple and a sintered glass frit air-inlet tube. The beaker was charged with 200 g (0.67 mole) of tall oil rosin acid and 56.3 g (0.67 mole) of sodium bicarbonate in 2000 ml of distilled water and stirred until an aqueous solution was formed. The tall oil rosin acid was obtained from Westvaco Chemicals and identified as Rosin S™. The solution was heated to 50° C. and charged with 0.1 g of iron sulfate, 85.7 g anhydrous hydrazine (2.68 moles) and an air sparge of about 800 ml/min. A Nalco defoamer was used as needed. The combination of heating and the reaction exotherm raised the reaction temperature to 70° C., where it was maintained for 3 hours with constant stirring and air sparge. The reaction mixture was cooled to room temperature, filtered and neutralized by the slow addition of concentrated hydrochloric acid to precipitate the reduced rosin acid which was dried in a vacuum oven at 110° C. and 29 inches Hg vacuum for 3 hours. Mass spectrometry showed a decrease in the 302 molecular weight rosin acid with an increase in 304 and 306 molecular weight, with infrared analysis showing complete retention of the carboxyl carbonyl function, and proton NMR analysis showing a 46 percent decrease in olefinic unsaturation. The product resin melted at 72° C.

EXAMPLE 2

A run was carried out under the conditions of Example 1, except the stainless beaker was charged with 150 grams (0.5 mole) tall oil rosin acid and 20 g (0.5 mole) of sodium hydroxide in 2000 ml of water. The same tall oil rosin acid was used as in Example 1. After heating to 50° C., the solution was charged with 0.1 g copper sulfate, 64 g (2 moles) anhydrous hydrazine and air sparge as the reaction mixture was heated to 80° C. for 3 hours. The reaction mixture was cooled, filtered and neutralized with concentrated hydrochloric acid, washed with water and vacuum-oven dried at 110° C. for 3 hours to give an amber resin melting at 70–87° C. Infrared analysis showed complete retention of the acid function, and proton NMR showed near quantitative decrease in olefinic unsaturation.

EXAMPLE 3

A run was done similar to Example 2, except the amount of anhydrous hydrazine was increased to 128 g (4 moles). Workup as in Example 2 gives an amber resin melting at 78–105° C., with infrared analysis showing retention of the carbonyl function, and NMR analysis showing near quantitative decrease in olefinic unsaturation.

EXAMPLE 4

A run was carried out similar to Example 2 except the rosin acid was replaced with tall oil with 50 g (~0.177 mole) of tall oil fatty acids, which contains 46.6 percent oleic acid, 33.9 percent linoleic acid, 6.9 percent conjugated diene acids, 13.2 percent other acids. Then, 0.177 mole (7.0 g) of NaOH in water was charged and stirred to put the oil in solution. The nonacid components were separated by phase separation. The acid salt solution was heated to 50° C. and charged with 0.1 g copper-sulfate and 22.6 g hydrazine (anhydrous) and the air sparge started. After 2 hours at 90° C., the mixture was cooled, filtered and neutralized with concentrated hydrochloric acid to give a white solid having a melting point range of from 55 to 65° C. GC shows reduction to predominantly stearic acid. Infrared analysis shows retention of the carboxylic acid carbonyl and loss of the cis and trans olefins. NMR shows an appreciable decrease of olefinic content.

What is claimed is:

1. A process for hydrogenating carbon-carbon double bonds of a water-soluble olefinically unsaturated carboxylic acid salt which comprises (a) combining an aqueous solution of an olefinically unsaturated carboxylic acid salt with
　　(1) an oxidant selected from the group consisting of oxygen, air and hydroperoxides;
　　(2) a reducing agent selected from hydrazine and hydrates thereof; and
　　(3) a metal ion activator;
　(b) heating the mixture to a temperature from 0° C. to the reflux temperature of the reaction mixture; and
　(c) neutralizing the pH of the reaction mixture.

2. The process of claim 1 wherein said water-soluble olefinically unsaturated carboxylic acid salt is derived from a carboxylic acid selected from the group consisting of a fatty acid, a rosin acid and mixtures thereof.

3. The process of claim 2 wherein said fatty acid is selected from the group consisting of oleic acid, 9,12-linoleic acid, 9,11-linoleic acid and 9,12,15-linolenic acid.

4. The process of claim 2 wherein said rosin acid is selected from the group consisting of abietic acid, levopimaric acid, neoabietic acid, palustric acid, dehydroabietic acid, pimaric acid, isopimaric acid, Δ-isopimaric acid, elliotinoic acid, sandaracopimaric acid and mixtures thereof.

5. The process of claim 1 wherein the olefinically unsaturated carboxylic acid salt is selected from the group consisting of sodium salts, potassium salts and lithium salts.

6. The process of claim 5 wherein the olefinically unsaturated carboxylic acid salt is a sodium salt.

7. The process of claim 1 wherein the concentration of the olefinically unsaturated carboxylic acid salt in the aqueous solution ranges from about 1 percent by weight to complete saturation.

8. The process of claim 1 wherein the mixture is heated to a temperature ranging from 0 to 300° C.

9. The process of claim 1 wherein the oxidant is air.

10. The process of claim 1 wherein the reducing agent is hydrazine.

11. The process of claim 1 wherein the metal ion activator is a salt of a metal selected from the group consisting of antimony, arsenic, bismuth, cerium, chromium, cobalt, copper, gold, iron, lead, manganese, mercury, molybdenum, nickel, osmium, palladium, platinum, silver and tin.

12. The process of claim 11 wherein the metal is selected from the group consisting of cobalt, copper, iron, lead, nickel, silver and tin.

* * * * *